US00PP17877P3

(12) United States Plant Patent
Meilland

(10) Patent No.: US PP17,877 P3
(45) Date of Patent: Jul. 24, 2007

(54) SHRUB ROSE PLANT NAMED 'MEIGALPIO'

(50) Latin Name: *Rosa hybrida*
Varietal Denomination: Meigalpio

(75) Inventor: Alain A. Meilland, Antibes (FR)

(73) Assignee: CP Delaware, Inc., Wilmington, DE (US)

( * ) Notice: Subject to any disclaimer, the term of this patent is extended or adjusted under 35 U.S.C. 154(b) by 0 days.

(21) Appl. No.: 11/213,813

(22) Filed: Aug. 30, 2005

(65) Prior Publication Data

US 2006/0005288 P1 Jan. 5, 2006

(51) Int. Cl.
*A01H 5/00* (2006.01)

(52) U.S. Cl. ..... Plt./108
(58) Field of Classification Search ..... Plt./108
See application file for complete search history.

(56) References Cited

PUBLICATIONS

Upov–rom Plant Variety Database 2005/05, GTI Jouve Retrieval Software, Citation for *Rosa* 'Meigalpio' one page.*

Meilland International a World of Roses [online] [retrieved on May 10, 2006]. Retrieved from the Internet. <http://www.meilland.com/> 2 pages.*

* cited by examiner

*Primary Examiner*—Kent Bell
*Assistant Examiner*—June Hwu
(74) *Attorney, Agent, or Firm*—Buchanan Ingersoll & Rooney PC

(57) ABSTRACT

A new and distinct variety of landscape shrub rose plant is provided which abundantly forms on a nearly continuous basis attractive small brilliant red-pink blossoms having good color stability. The plant exhibits a low, compact and bushy growth habit. Good disease tolerance including resistance to Black Spot has been displayed. The attractive dark green foliage contrasts nicely with the red-pink blossom coloration. The new variety is particularly well suited for growing as attractive ornamentation in the landscape.

1 Drawing Sheet

Figures 1, 2, 3, 4, 5, 6, 7, 8, 9, 10, 11, 12, 13, 14, 15, 16, 17:
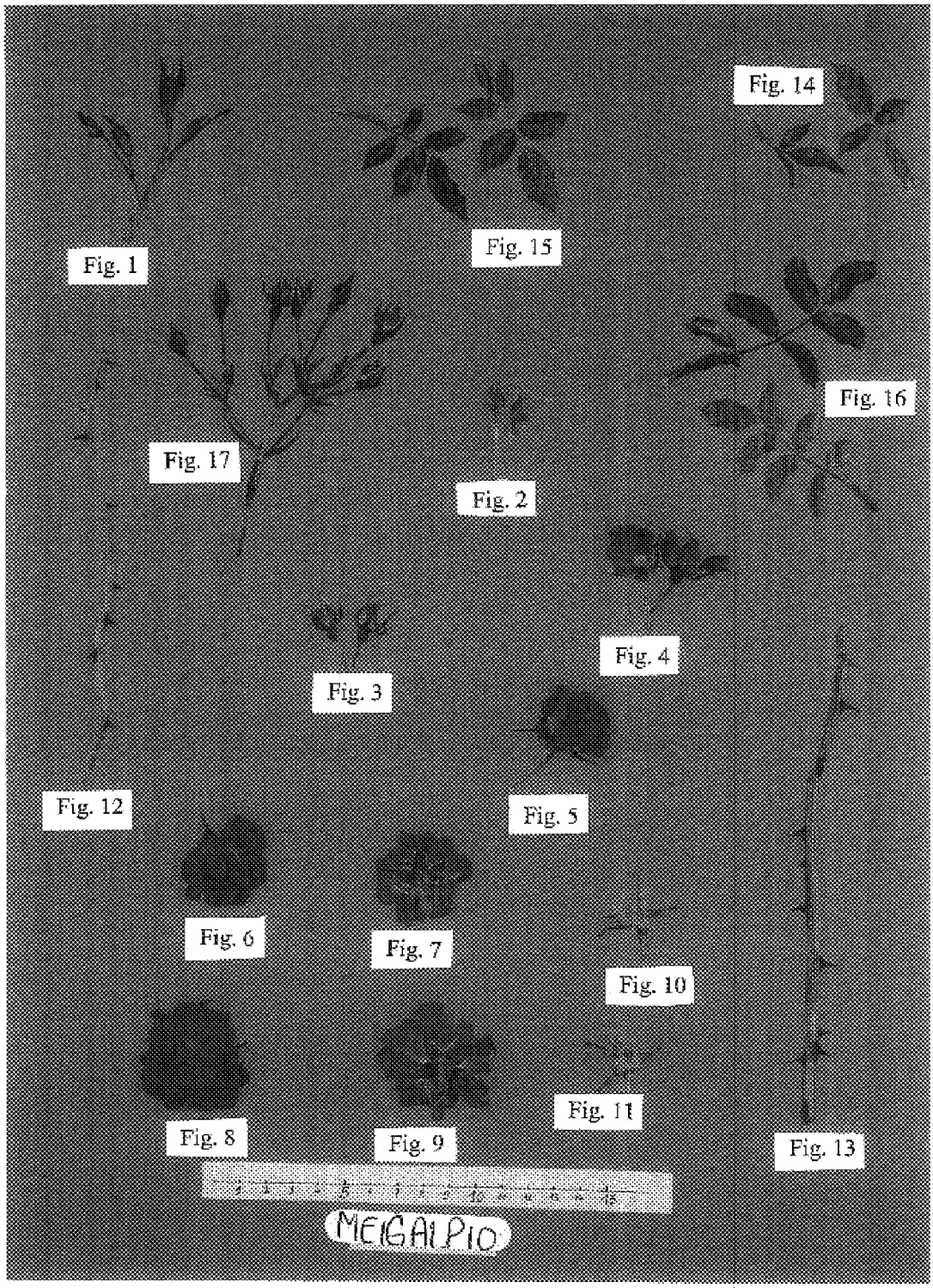

Botanical/commercial classification: *Rosa hybrida*/Shrub Rose.

Varietal denomination: cv. Meigalpio.

SUMMARY OF THE INVENTION

The new variety of *Rosa hybrida* shrub rose plant was created by artificial pollination wherein two parents were crossed which previously had been studied in the hope that they would contribute the desired characteristics. The female parent (i.e., the seed parent) was a non-patented and unnamed seedling formed by the cross of 'The Fairy' variety (non-patented in the United States) and the 'Kormax' variety (non-patented in the United States). The male parent (i.e., the pollen parent) was a non-patented and unnamed seedling formed by the cross of another non-patented and unnamed seedling and the 'Morpapplay' variety (U.S. Plant Pat. No. 6,548). The parentage of the new variety can be summarized as follows:

('The Fairy'×'Kormax')×(Unnamed Seedling×'Morpapplay').

The seeds resulting from the above pollination were sown and small plants were obtained which were physically and biologically different from each other. Selective study resulted in the identification of a single plant of the new variety.

It was found that the new variety of the present invention (a) exhibits a low, compact and bushy growth habit, (b) abundantly forms in clusters on a nearly continuous basis attractive small brilliant red-pink blossoms having a good color stability, (c) forms very dense dark green foliage having a semi-glossy aspect that contrasts well with the blossom coloration, and (d) is particularly well suited for growing as attractive ornamentation in the landscape.

The tolerance to diseases is good. During observations to date the plant has been resistant to Black Spot.

The new variety well meets the needs of the horticultural industry and can be grown to advantage in parks and gardens where attractive ornamentation is desired.

The new variety can be readily distinguished from its ancestors. For instance, 'The Fairy' variety forms light pink blossoms, the 'Kormax' variety forms considerably larger red blossoms having only six petals, and the 'Morpapplay' variety forms dark orange-red blossoms having a bright yellow eye.

The new variety of the present invention also can be readily distinguished from the 'Ruimired' variety (U.S. Plant Pat. No. 5,770) and the 'Meirutral' variety (U.S. Plant Pat. No. 7,021). The blossoms of the 'Ruimired' variety display a lesser developed basal color spot. The 'Meirutral' variety displays a dissimilar erect growth habit and forms blossoms that are darker in coloration.

The new variety has been found to undergo asexual propagation in France by a number of routes, including budding, grafting, and cuttage. Asexual propagation by the above-mentioned techniques in France has shown that the characteristics of the new variety are stable and are strictly transmissible by such asexual propagation from one generation to another.

The new variety has been named 'Meigalpio'.

BRIEF DESCRIPTION OF THE PHOTOGRAPH

The accompanying photograph shows as nearly true as it is reasonably possible to make the same, in a color illustration of this character, typical specimens of the plant parts of the new variety. The rose plants of the new variety were approximately eighteen months of age and were observed during August while budded on *Rosa froebelli* understock and growing outdoors at Le Cannet des Maures, Var, France. Dimensions in centimeters are indicated at the bottom of the photograph.

FIG. 1—illustrates a specimen of a young shoot;

FIG. 2—illustrates a specimen of a floral bud before the opening of the sepals;

FIG. 3—illustrate specimens of two floral bud at the opening of the sepals;

FIG. 4—illustrates a specimen of a floral bud at the opening of the petals;

FIG. 5—illustrates a specimen of a flower in the course of opening;

FIG. 6—illustrates a specimen of an open flower—plan view—obverse;

FIG. 7—illustrates a specimen of an open flower—plan view —reverse;

FIG. 8—illustrates a specimen of a fully open flower—plan view —obverse;

FIG. 9—illustrates a specimen of a fully open flower—plan view —reverse;

FIG. 10—illustrates a specimen of a floral receptacle showing the arrangement of the stamens and pistils;

FIG. 11—illustrates a specimen of a floral receptacle showing the arrangement of the pistils (stamens removed);

FIG. 12—illustrates a specimen of a flowering stem;

FIG. 13—illustrates a specimen of a main branch;

FIG. 14—illustrates specimens of leaves with three leaflets—plan view—upper and under surfaces;

FIG. 15—illustrates specimens of leaves with five leaflets—plan view—upper and under surfaces;

FIG. 16 —illustrates specimens of leaves with seven leaflets —plan view—upper and under surfaces; and FIG. 17—illustrates a cluster of buds.

DETAILED DESCRIPTION

The chart used in the identification of the colors is that of The Royal Horticultural Society (R.H.S. Colour Chart). The description is based on the observation of eighteen month-old plants during August while budded on *Rosa froebelli* understock and growing outdoors at Le Cannet des Maures, Var, France.

Class: Landscape Shrub.

Plant:

*Height.*—Approximately 30 to 40 cm on average at the end of the growing season.

*Width.*—Approximately 40 to 45 cm on average at the end of the growing season.

*Habit.*—Low, bushy and compact.

Branches:

*Color.*—Young stems: smooth with some thorns and prickles, and near Green Group 143C. Adult wood: smooth with some thorns and prickles, and near Yellow-Green Group 144B.

*Thorns.*—Size and quantity: on 16 cm of young stems approximately 14 on average approximately 0.6 cm in length; and on 18 cm of adult stems approximately 22 on average approximately 0.6 cm in length. Color: near Greyed-Orange Group 176A on young stems, and near Greyed-Orange Group 176B on adult stems. Configuration: very longish pointed and curved downwards on the upper surface and slightly concave on the under surface with an obovate base.

*Small prickles.*—Size and quantity: on 16 cm of young stems approximately 6 on average approximately 0.3 cm in length. Color: near Greyed-Yellow Group 161A suffused with Greyed-Orange Group 176B. Configuration: possess an obovate base.

Leaves:

*Size.*—A seven-leaflet leaf commonly measures approximately 7.5 cm in length on average, and approximately 4.8 cm in width on average.

*Stipules.*—Adnate, pectinate, smooth, broad, approximately 2.5 cm in length on average, approximately 0.8 cm in width on average, near Yellow-Green Group 147A on the upper surface, and near Yellow-Green Group 146B on the under surface.

*Petioles.*—Upper surface: non-glandular and near Yellow-Green Group 147B in coloration. Under surface: bears a few prickles and near Yellow-Green Group 146C in coloration. Length: approximately 0.3 cm for the terminal leaflet.

*Petiole rachis.*—Upper surface: non-glandular, and near Yellow-Green Group 147B in coloration. Under surface: with a few prickles, and near Yellow-Green Group 146B in coloration.

*Leaflets.*—Number: 3, 5 and 7 (most often). Shape: generally oval with an obtuse base and a pointed tip. Size: the terminal leaflets commonly are approximately 2.6 cm in length on average, and approximately 1.2 cm in width on average. Serration: single and fine. Texture: firm and consistent. General appearance: very dense, dark green with a semi-glossy aspect. Color (young foliage): Upper surface: near Yellow-Green Group 147A. Under surface: near Yellow-Green Group 146B. Color (adult foliage): Upper surface: near Yellow-Green Group 147A. Under surface: near Yellow-Green Group 146B.

Inflorescence:

*Number of flowers.*—Commonly approximately 6 to 15 flowers per stem in a cluster.

*Peduncle.*—Rigid, firm and well supports blossoms, near Yellow-Green Group 144A in coloration, glandular, approximately 2.5 cm in length on average, and approximately 0.1 cm in diameter on average.

*Sepals.*—Upper surface: tomentose consistent and near Green Group 138B and 138C in coloration. Under surface: glandular and near Green Group 143A in coloration. Configuration: narrow with a longish point and uncurved at the base. Size: approximately 1.1 cm in length on average, and approximately 0.8 cm in width at the widest point on average.

*Buds.*—Shape: conical. Size: small. Length: approximately 1.1 cm on average. Width: approximately 0.8 cm at the widest point on average. Color: Upper surface: near Red Group 54B amply suffused with Red Group 45B as the calyx breaks. Under surface: near Red Group 54B amply with Red Group 45B as the calyx breaks. Basal petal spot: near Yellow Group 8B on both surface.

*Flower.*—Shape: generally cup-shaped. Diameter: approximately 4 cm on average. Color (in course of opening): Upper surface: Red-Purple Group 57A and amply suffused with Red-Purple Group 58A. Under surface: near Red-Purple Group 57A and amply suffused with Red-Purple Group 58A. Basal petal spot: near Yellow Group 6D. Color (open flower): Upper surface: near Red-Purple Group 57A and amply suffused with Red-Purple Group 58A. Under surface: near Red-Purple Group 57A and amply suffused with Red-Purple Group 58A. Basal petal spot: near Yellow Group 6D. Color stability: very good. Fragrance: none. Lasting quality: the blossoms commonly last approximately 2 to 3 weeks on the plant on average depending upon the environment conditions. Petal number: approximately 14 on average under normal growing conditions. Petal size: approximately 1.7 cm in length on average, and approximately 1.5 cm in width on average. Petal texture: smooth. Petaloids: small and present at center. Petal shape: rounded tip and obtuse base. Petal arrangement: imbricated. Petal drop: good with the petals commonly detaching cleanly before drying. Stamen number: approximately 30 on average. Anthers: regularly arranged around the styles, the approximately 0.1 cm in size on average, and near Greyed-Orange Group 166A in coloration. Pollen: sparsely present and near Greyed-Orange Group 166A in coloration. Filaments: near Yellow Group 12C in coloration, and approximately 0.4 cm in length on average. Pistils: approximately 15 on average. Stigmas: near Greyed-Green Group 160B in coloration, and approximately 0.1 cm in size. Styles: near Greyed-Green Group 191C in coloration, and approximately 0.3 cm in length on average. Receptacle: glandular, near Yellow-Green Group 144A in coloration, and pitcher-shaped in longitudinal section. The length commonly is approximately 0.5 cm on average and the width commonly is approximately 0.3 cm on average. Hips: none observed.

Development:

*Vegetation.*—Medium.

*Blooming.*—Abundant and nearly continuous.

*Resistance to diseases.*—Good disease tolerance and resistant to Black Spot during observations to date.

*Aptitude to bear fruit.*—None observed during observations to date.

*Hardiness.*—Good, performs well in USDA Hardiness Zone Nos. 6B and 7A.

*Resistance to heat.*—Produces blossoms in the Central Valley of California, U.S.A. during the summer.

I claim:

1. A new and distinct landscape shrub rose plant characterized by the following combination of characteristics:

(a) exhibits a low, compact and bushy growth habit, (b) abundantly forms in clusters on a nearly continuous basis attractive small brilliant red-pink blossoms having good color stability, (c) forms very dense dark green foliage having a semi-glossy aspect that contrasts well with the blossom coloration, and (d) is particularly well suited for growing as attractive ornamentation in the landscape;

substantially as herein shown and described.

* * * * *

MEIGALPIO